United States Patent [19]

Suzukamo et al.

[11] Patent Number: 4,487,956

[45] Date of Patent: Dec. 11, 1984

[54] MENTHYL 2,2-DIMETHYLCYCLOPROPANECARBOXYLATE AND RESOLUTION OF THE SAME

[75] Inventors: Gohfu Suzukamo, Ibaraki; Yoji Sakito, Takarazuka, both of Japan

[73] Assignee: Sumitomo Chemical Company, Limited, Osaka, Japan

[21] Appl. No.: 533,635

[22] Filed: Sep. 19, 1983

[30] Foreign Application Priority Data

Jul. 20, 1983 [JP] Japan .................. 58-133043

[51] Int. Cl.³ .......................... C07C 69/74
[52] U.S. Cl. ................................ 560/124
[58] Field of Search ....................... 560/124

[56] References Cited

FOREIGN PATENT DOCUMENTS 51023 4/1980 Japan .
1260847 1/1972 United Kingdom .

OTHER PUBLICATIONS

Andrist, Chem. Abst., 89: 129076w (1978).
Eliel, Stereochemistry of Carbon Compounds," pp. 49-63 (1962).

Primary Examiner—Michael L. Shippen
Attorney, Agent, or Firm—Stevens, Davis, Miller & Mosher

[57] ABSTRACT

An ester obtained from 2,2-dimethylcyclopropanecarboxylic acid and optically active menthol, represented by the formula,

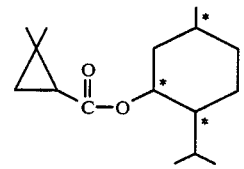

is effectively resolved into diastereomers, which upon hydrolysis give optically active 2,2-dimethylcyclopropanecarboxylic acid.

Unnecessary diastereomeric ester, remained after resolution, can be epimerized selectively on the acid moiety.

Combination of the resolution and the epimerization provides an efficient method for production of optically active 2,2-dimethylcyclopropanecarboxylic acid.

8 Claims, No Drawings

MENTHYL 2,2-DIMETHYLCYCLOPROPANECARBOXYLATE AND RESOLUTION OF THE SAME

The present invention relates to a method for producing an optically active carboxylic acid and its optically active menthyl ester represented by the formula,

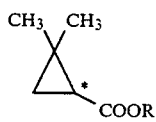

wherein R represents a hydrogen atom or an optically active menthyl group, by resolving an ester obtained from 2,2-dimethylcyclopropane-1-carboxylic acid and optically active menthol represented by the formula (I),

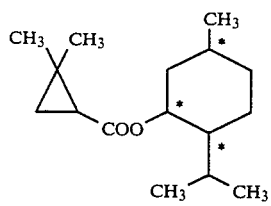

into the optical isomers by chromatography or fractional crystallization, and hydrolyzing the isomer obtained if necessary, and further relates to the ester represented by the foregoing formula (I).

An object of the present invention is a novel 2,2-dimethylcyclopropane-1-carboxylic acid derivative and is to obtain said carboxylic acid therefrom in optically active form in a good efficiency.

2,2-Dimethylcyclopropane-1-carboxylic acid is an important compound as an intermediate for agricultural chemicals and medicines. For example, it is well known that the ester of said carboxylic acid with an alcohol such as substituted 2-cyclopentenone-4-ol, substituted furfuryl alcohol or the like, exhibits the similar actions as those of esters, called a pyrethroid insecticides which are useful as rapid knock-down insecticides with low mammalian toxicity (specification of B.P. No. 1,260,847).

Said acid is also used as a component of inhibitors against enzymes causing decomposition in vivo of β-lactam type antibiotics [Kagaku to Seibutsu, 19, 204 (1981)].

In many cases, the use of optically active compounds is desirable for such uses.

The present invention provides a novel compound which is important to advantageously produce this useful optical isomer of 2,2-dimethylcyclopropane-1-carboxylic acid and a method for producing said compound.

2,2-Dimethylcyclopropane-1-carboxylic acid is obtained as a racemate, i.e. (±)-form, by usual synthetic methods. In order to obtain desired optical isomers, therefore, there was a further necessity to carry out resolution of said racemate with optically active organic bases, etc.

As a method for producing an optically active 2,2-dimethylcyclopropanecarboxylic acid, a method of optical resolution of dl-2,2-dimethylcyclopropanecarboxylic acid is known as described below.

(1) Resoluton with quinine [Japanesse Patent Application Kokai (Laid-open) No. 51023/1980], and (2) Resolution with d- or l-α-phenethylamine (specification of B.P. No. 1,260,847).

The former method, however, has a problem that quinine, very expensive as well as not available stably, should be used as a resolving agent, and besides that the yield is low. The latter method also has a problem that there is obtained d- or l-2,2-dimethylcylopropanecarboxylic acid only of such a low optical purity that the optical rotation is +65° for the d-form and −72° for the l-form which corresponds to 49% and 55% enantiomer excess, respectively. Either of these methods, therefore, may not be said to be a one for obtaining d- or l-2,2-dimethylcyclopropanecarboxylic acid of high optical purity advantageously in industry.

The present inventors found that said novel compound represented by the foregoing formula (I), i.e. an ester obtained from 2,2-dimethylcyclopropane-1-carboxylic acid and optically active menthol, is a derivative which is favorable to produce an optically active 2,2-dimethylcyclopropane-1-carboxylic acid in high efficiency, and after a further extensive study, completed the present invention. According to the present invention, it becomes possible to obtain one of the enantiomer of 2,2-dimethylcyclopropanecarboxylic acid through resolution of the ester represented by the formula (I), whose acid part may be either dl-form of said carboxylic acid or a mixture of the d- and l-isomers thereof in optional proportions. As a separation method, chromatography may be used. Further, under certain proper conditions, fractional crystallization of one of the diastereomers is carried out very advantageously. From the one optically active menthyl ester of said carboxylic acid thus obtained, an optically active 2,2-dimethylcyclopropane-1-carboxylic acid can be obtained by hydrolysis in a high purity and with its steric configuration kept unchanged. As the other diastereomeric ester can be epimerized at $C_1$ position of acid part if necessary, repetition of the above procedure makes it possible to produce said one optically active 2,2-dimethylcyclopropane-1-carboxylic acid in a good efficiency. This can be shown by the following scheme (An example using l-menthol is illustrated. When d-menthol is used, opposite enantiomer is obtained in each case).

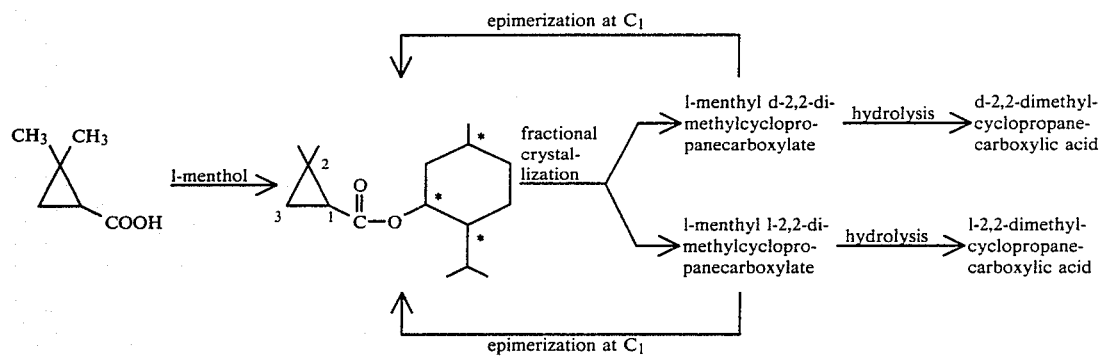

The present invention will be explained in detail hereinafter. Symbols, "d-" and "l-", used herein express the optical isomerism of the acid and alcohol constituting the ester, not that of the ester.

The menthyl ester of 2,2-dimethylcyclopropane-1-carboxylic acid can be synthesized, for example, by reacting the acid halide or acid anhydride of said carboxylic acid with l- or d-menthol.

Said carboxylic acid halide or acid anhydride is obtained by usual method.

The ester, represented by the formula (I), is synthesized by reacting the thus-obtained acid halide or acid anhydride with d- or l-menthol at $-20°$ C. to $60°$ C. As the solvent, those which do not take part in the reaction such as saturated hydrocarbons, aromatic ones, halogenated ones, etc. may be used. As need arises, organic bases such as pyridine, triethylamine, etc. are used as an acid scavenger.

Another method for producing said ester involves reaction of menthyl diazoacetate with isobutylene in the presence of copper catalyst.

The menthyl ester of 2,2-dimethylcyclopropanecarboxylic acid has four diastereomers. Of these, both the l-menthyl ester of d-acid and the d-menthyl ester of l-acid take a crystalline form in the vicinity of room temperature, while both the d-menthyl ester of d-acid and the l-menthyl ester of l-acid take an oily form in the vicinity of room temperature. That is, the diastereomeric ester obtained from the racemic carboxylic acid and l-menthol contains the crystalline diastereomer of d-acid with l-menthol, while that obtained from the racemic carboxylic acid and d-menthol contains the crystalline diastereomer of l-acid with d-menthol. By separating the oily part from the crystalline part, therefore, optical resolution for the objective isomer can be carried out advantageously. Referring further to the separation of isomer, the separation and purification of diastereomer may be carried out by chromatography, but fractional crystallization is more preferred. Fractional crystallization may be carried out in the presence or absence of solvent, but generally, a solvent is used. As the solvent used at that time, those of which the temperature difference causes a great difference in the solubility of said crystalline part are preferred. For example, saturated hydrocarbons (e.g. hexane, heptane), alcohols (e.g. methanol, ethanol), aqueous alcohols and mixtures thereof are preferred. The crystallization temperature is preferably about $40°$ C. to the vicinity of $0°$ C. in terms of operation.

The ester of said optically active carboxylic acid thus obtained is hydrolyzed under a basic aqueous condition if necessary to give the objective compound, d-2,2-dimethylcyclopropane-1-carboxylic acid or l-2,2-dimethylcyclopropane-1-carboxylic acid without loss of optical purity. As the base used in the hydrolysis, those which are commonly used in the hydrolysis of a carboxylic acid ester are used, and their amount used is 1 to 4 moles based on 1 mole of the ester. The reaction is carried out at $50°$ C. to a refluxing temperature. The reaction time relates to the reaction condition, but generally, periods of 0.5 to 10 hours are sufficient. As the solvent used, water and its mixtures with organic solvents (e.g. methanol, ethanol) may be used, and surface active agents may also be added.

After reaction, the optically active menthol is recovered as a neutral product, and then on acidifying and extracting the aqueous layer, 2,2-dimethylcyclopropane-1-carboxylic acid retaining optical purity can be obtained.

The diastereomeric ester rich in the one of the diastereomer obtained by optical resolution can selectively be epimerized at its carboxylic acid moiety by the method described below: The menthyl ester of said carboxylic acid can be epimerized in good efficiency without being accompanied by side reaction by treatment with an alkali metal, alkali metal hydride, dispersion thereof or alkali metal alcoholate. Referring to the epimerization in more detail, this method is epimerization of said carboxylic acid ester using as catalyst alkali metals (e.g. lithium, sodium, potassium) or alloys of two or more alkali metals such as sodium-potassium. In this case, employment of the so-called alkali metal dispersions, as obtained by finely pulverizing said alkali metal in a medium, is well known. Particularly, by using dispersions in a state wherein an alkali metal has been dispersed in a medium such as toluene, xylene, vaseline, naphthalene, anthracene, mineral oil or the like, or in a state wherein said alkali metal has been supported on a porous carrier such as alumina, silica gel, activated carbon or the like, the reaction proceeds more smoothly. Further, in the method of the present invention, the hydride of said alkali metal, that is, alkali metal hydrides such as lithium hydride, sodium hydride, potassium hydride, etc. may also be used as the catalyst. Any form of alkali metal hydride may be used, but the effect can further be raised by using fine powders of the hydride. Alkali metal hydride dispersed in a mineral oil is in a practical use, and the reaction can satisfactorily be carried out without removing such dispersing agent.

Examples of alkali metal alcoholate include for example sodium methylate, sodium ethylate, potassium tert-butylate and the like.

The necessary amount of catalyst varies with the ratio of optical isomers of the material and reaction condition, but it is generally within a range of 1/1000 to ½ equivalent, preferably 1/100 to 1/5 equivalent based on the ester to be treated.

A solvent is not particularly necessary, but when it is used, those which do not inhibit the epimerization of the present invention are selected. Such solvents include for example saturated hydrocarbons, aromatic ones, ethers and the like. The mixture of these solvents may also be used.

The reaction of the epimerization can be carried out independently of external pressure, and it will proceed under any condition of normal pressure and raised pressure. In order to protect the reaction system from moisture, it is preferred to carry out the reaction in an inert gas atmosphere such as nitrogen or argon.

The reaction temperature is within a range of generally 20° C. to 200° C., preferably 50° C. to 170° C.

The reaction time varies with reaction conditions such as the amount of catalyst, heating temperature, etc., but generally, the object can be attained in several minutes to several ten hours. From the epimerized ester thus obtained, the objective optically active 2,2-dimethylcyclopropane-1-carboxylic acid can be obtained by applying the aforementioned resolution and purification of the ester.

As described above in detail, the useful optically active 2,2-dimethylcyclopropane-1-carboxylic acid derivative can be produced in a good efficiency from the ester obtained from 2,2-dimethylcyclopropane-1-carboxylic acid and optically active menthyl ester.

Next, the method of the present invention will be illustrated with reference to the following examples.

EXAMPLE 1

To 5.0 g of dl-2,2-dimethylcyclopropane-1-carboxylic acid in a 50-ml flask were added 5.0 g of n-hexane and one drop of dimethylformamide, and the mixture was heated to 70° C. Thereafter, a mixed solution of 7.82 g of thionyl chloride and 2.0 g of n-hexane was added dropwise from a dropping funnel at the same temperature with stirring. After stirring for further 3 hours at the same temperature, the solvent was removed under reduced pressure, and then the residual liquor was distilled to obtain 5.23 g of dl-dimethylcyclopropane-1-carboxylic acid chloride at a boiling point of 58° to 60° C./40 mmHg.

To a 100-ml flask were added 5.6 g of l-menthol, 25 g of methylene chloride and 4.3 g of pyridine, and a mixed solution of 5.0 g of the above acid chloride distillate and 5.0 g of methylene chloride was added dropwise from a dropping funnel while stirring the contents of the flask with ice-cooling. After stirring for 1 hour at the same temperature and being allowed to stand at room temperature overnight, the reaction solution was washed with 9.2 g of 10% aqueous hydrochloric acid solution. The organic layer was washed with water, 5.0 g of 1.5% aqueous sodium hydroxide solution and water in this order, and concentrated under reduced pressure to obtain 8.5 g of a residual liquor.

On distilling the residual liquor, 8.3 g of l-methyl dl-2,2-dimethylcyclopropane-1-carboxylate was obtained at a boiling point of 68° to 72° C./0.1 mmHg. This product crystallized, and its melting region was 55° to 61° C. and its optical rotation, $[\alpha]_D^{26}$, was $-60.5°$ (c=1.0, EtOH).

EXAMPLE 2

6.0 Grams of the l-methyl dl-2,2-dimethylcyclopropane-1-carboxylate obtained in Example 1 was added to a 50-ml flask and fractionally crystallized from n-hexane to obtain 2.1 g of l-menthyl d-2,2-dimethylcyclopropane-1-carboxylate. On measuring the ratio of optical isomers of this ester by gas chromatography, it was found that the content of l-menthyl d-2,2-dimethylcyclopropane-1-carboxylate was 97.2% and that of l-methyl l-2,2-dimethylcyclopropane-1-carboxylate was 2.8%. On measuring the filtrate similarly, the former content was 24.5% and the latter one was 75.5%.

On fractionally crystallizing this crystal again, l-menthyl d-2,2-dimethylcyclopropane-1-carboxylate of which the ratio of optical isomers was 100:0, was obtained. This product had a melting point of 74° to 75.5° C. and an optical rotation, $[\alpha]_D^{26}$, of $+1.2°$ (c=0.965, EtOH).

EXAMPLE 3

To a 25-ml flask were added 0.5 g of the l-menthyl d-2,2-dimethylcyclopropane-1-carboxylate obtained in Example 2 and 1.2 g of 10% aqueous sodium hydroxide solution, and the mixture was stirred under reflux for 2 hours.

The reaction solution was diluted with water, and the neutral product was twice extracted with methylene chloride. After acidifying the aqueous layer with hydrochloric acid, the carboxylic acid was twice extracted with methylene chloride. The organic layer was washed with water and dried over sodium sulfate, and the solvent was removed by evaporation to obtain 0.21 g of a residual liquor. This liquor was distilled on a Kugel Rohr to obtain 0.20 g of a distillate at 135° to 140° C./20 mmHg.

This product was confirmed to be d-2,2-dimethylcyclopropane-1-carboxylic acid by gas chromatography and infrared absorption spectrum, and its optical rotation, $[\alpha]_D^{25}$, was $+131.2°$ (c=2.0, EtOH).

The extract containing the neutral product was washed with water, and the solvent was removed by evaporation to obtain 0.30 g of a colorless crystal. It was found by gas chromatography and infrared absorption spectrum that this product was l-menthol.

EXAMPLE 4

To a 25-ml flask were added 5.0 g of l-menthyl dl-2,2-dimethylcylopropane-1-carboxylate and 20 g of methanol, and the mixture was heated to 50° C. to turn into a homogeneous solution. The solution was then slowly cooled and kept ice-cooled, and the deposited crystal was collected by filtration. On drying and weighing the crystal, the weight was 1.95 g. On measuring the ratio of optical isomers of this product by gas chromatography, it was found that the content of d-isomer was 93.4% and that of l-isomer was 6.6%. On measuring the ratio of optical isomers of the ester in the filtrate similarly, it was found that the content of d-isomer was 22.3% and that of l-isomer was 77.7%.

EXAMPLE 5

To a 25-ml flask were added, while passing a nitrogen stream therethrough, 0.5 g of said carboxylic acid ester comprising 24.9% of l-menthyl d-2,2-dimethylcyclopropane-1-carboxylate and 76.1% of l-menthyl l-2,2-dimethylcyclopropane-1-carboxylate and 0.022 g of potassium tert-butylate, and the mixture was kept at 120° C. for 1 hour. Thereafter, the reaction solution was distilled as it was on a Kugel Rohr to obtain 0.48 g of a colorless and transparent oily product. This product crystallized in a little while, and it was found by gas-chromatographic analysis that this product comprised 48.0% of l-menthyl d-2,2-dimethylcyclopropane-1-carboxylate and 52.0% of l-menthyl l-2,2-dimethylcyclopropane-1-carboxylate. This product had an optical rotation, $[\alpha]_D^{28}$, of $-63.9°$ (c=1.04, EtOH) and a melting region of 55° to 60° C.

EXAMPLE 6

In the same manner as in Example 1, 5.2 g of dl-2,2-dimethylcyclopropane-1-carboxylic acid chloride was obtained from 5.0 g of dl-2,2-dimethylcyclopropane-1-carboxylic acid.

To a 100-ml flask were added 5.6 g of d-menthol, 25 g of methylene chloride and 4.3 g of pyridine, and in the same manner as in Example 1, the resulting mixture was reacted with a mixed solution of 5.0 g of the above acid chloride and 5.0 g of methylene chloride to obtain 8.3 g of d-menthyl dl-2,2-dimethylcyclopropane-1-carboxylate. This ester had the following properties: Boiling point, 68° to 72° C./0.1 mmHg; melting region, 54° to 61° C.; and optical rotation, $[\alpha]_D^{26}$, $+60.2°$ (c=1.0, EtOH).

EXAMPLE 7

6.0 Grams of d-menthyl dl-2,2-dimethylcyclopropane-1-carboxylate obtained in Example 6 was fractionally crystallized from n-hexane in the same manner as in Example 2 to obtain 2.0 g of d-menthyl l-2,2-dimethylcyclopropane-1-carboxylate. The ratio of optical isomers of this ester was l:d (optical purity of said carboxylic acid moiety)=97.0:3.0. That of the filtrate was 24.4:75.6. On recrystallizing again this product from n-hexane, d-menthyl l-2,2-dimethylcyclopropane-1-carboxylate, of which the ratio of optical isomers was 99.8:0.2, was obtained. This product had a melting point of 74° to 75.5° C. and an optical rotation, $[\alpha]_D^{26}$, of $-1.2°$ (c=1.0, EtOH).

EXAMPLE 8

To 2.7 g of l-menthyl dl-2,2-dimethylcyclopropane-1-carboxylate was added 3.0 ml of 30% aqueous methanol solution, and the mixture was stirred and suction-filtered.

The crystal part was washed with two 1.0 ml portions of 30% aqueous methanol solution and filtered. The washings were combined with the filtrate obtained above. The yield of the crystal part was 1.2 g, and the ratio of optical isomers (optical purity of said carboxylic acid moiety) obtained by gas chromatography was d:l=95.4:4.6. On concentrating the filtrate, 1.5 g of an oily product was obtained. Gas-chromatographic analysis showed that the ratio of said optically isomeric carboxylic acids of this product was d:l=13.7:86.3.

What is claimed is:

1. A method for producing optically active 2,2-dimethylcyclopropanecarboxylic acid and its derivative which comprises resolving an ester obtained from 2,2-dimethylcyclopropane-1-carboxylic acid and optically active menthol represented by the formula,

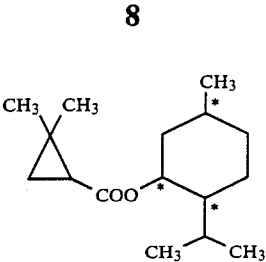

into the optical isomers by chromatography or fractional crystallization, and hydrolyzing the isomer obtained, if necessary, to obtain an optically active carboxylic acid or its optically active menthyl ester represented by the formula,

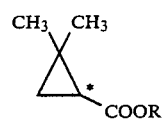

wherein R represents a hydrogen atom or an optically active menthyl group.

2. A method according to claim 1, wherein the optically active menthol is l-menthol.

3. A method for producing optically active 2,2-dimethylcyclopropanecarboxylic acid and its derivative which comprises treating an ester obtained from 2,2-dimethylcyclopropane-1-carboxylic acid and optically active menthol represented by the formula,

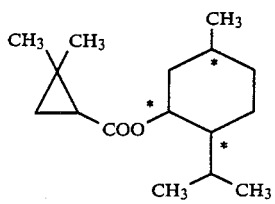

by chromatography or fractional crystallization to separate one optically active carboxylic acid ester, epimerizing the other diastereomeric ester by means of a base selected from alkali metal alcoholates, alkali metals and alkali metal hydrides, resolving the epimerized ester into each optical isomer by applying again chromatography or fractional recrystallization, and hydrolyzing the isomer obtained, if necessary, to obtain an optically active carboxylic acid or its optically active menthyl ester represented by the formula,

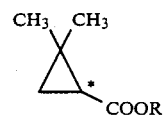

wherein R represents a hydrogen atom or an optically active menthyl group.

4. A method according to claim 3, wherein the optically active menthol is l-menthol.

5. An ester obtained from 2,2-dimethylcyclopropane-1-carboxylic acid and optically active menthol represented by the formula,

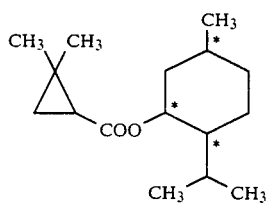
6. A compound according to claim 5, wherein the optically active menthol is l-menthol.
7. l-Menthyl d-2,2-dimethylcyclopropanecarboxylate.
8. d-Menthyl l-2,2-dimethylcyclopropanecarboxylate.
* * * * *